(12) United States Patent
Mak et al.

(10) Patent No.: US 11,293,743 B2
(45) Date of Patent: Apr. 5, 2022

(54) TEXTURE ANALYZER

(71) Applicant: AMETEK, INC., Berwyn, PA (US)

(72) Inventors: Alex Mak, Canton, MA (US); Arief Raja, Bangalore (IN); Charles Falzarano, Lakeville, MA (US); Shali Avidzba, Sudbury, MA (US); Kerri Topham, Attleboro, MA (US)

(73) Assignee: AMETEK, INC., Berwyn, PA (US)

( * ) Notice: Subject to any disclaimer, the term of this patent is extended or adjusted under 35 U.S.C. 154(b) by 346 days.

(21) Appl. No.: 16/715,336

(22) Filed: Dec. 16, 2019

(65) Prior Publication Data

US 2020/0200521 A1 Jun. 25, 2020

Related U.S. Application Data

(60) Provisional application No. 62/782,878, filed on Dec. 20, 2018.

(51) Int. Cl.
*G01B 5/28* (2006.01)

(52) U.S. Cl.
CPC .................................... *G01B 5/28* (2013.01)

(58) Field of Classification Search
CPC ........................................................ G01B 5/28
USPC ............................................................ 33/551
See application file for complete search history.

(56) References Cited

U.S. PATENT DOCUMENTS

| | | | |
|---|---|---|---|
| 4,736,208 A * | 4/1988 | Schmidt | G01B 7/28 346/33 R |
| 5,629,489 A | 5/1997 | Hipkiss et al. | |
| 6,077,822 A † | 6/2000 | Dyrsting | |
| 6,508,132 B1 | 1/2003 | Lohr et al. | |
| 8,117,892 B2 | 2/2012 | Kawazoe et al. | |
| 8,151,638 B2 | 4/2012 | Erlenkeuser et al. | |

(Continued)

FOREIGN PATENT DOCUMENTS

| | | |
|---|---|---|
| EP | 2331931 B1 | 3/2017 |
| JP | 4164682 B2 | 10/2008 |

(Continued)

OTHER PUBLICATIONS

Shimadzu EZ Test, downloaded from https://www.shimadzu.com/an/test/universal/eztest.html, 2012, 20 pages.

(Continued)

*Primary Examiner* — George B Bennett
(74) *Attorney, Agent, or Firm* — RatnerPrestia (57) ABSTRACT

A texture analyzer having a support structure including a base plate, a carriage support, and a moveable carriage that receives a load cell module; a fixture to receive a sample between the base plate and the load cell module; a memory storing support structure and load cell module deflection parameters; and a processor. The processor is configured to identify the load cell module, retrieve the support structure deflection parameters and one of multiple load cell module deflection parameters, obtain raw measurement signals from the load cell module, and refine the raw measurement signals to compensate for deflection in the load cell module using the retrieved load cell module deflection parameters and support structure deflection parameters.

10 Claims, 6 Drawing Sheets

(56) References Cited

U.S. PATENT DOCUMENTS

| | | | | |
|---|---|---|---|---|
| 8,191,408 | B2* | 6/2012 | Igasaki | G01B 3/008 |
| | | | | 73/105 |
| 8,398,454 | B2* | 3/2013 | Njegovan | G01B 5/28 |
| | | | | 451/5 |
| 8,925,367 | B2* | 1/2015 | Omori | G01B 5/201 |
| | | | | 73/1.81 |
| 9,074,865 | B2* | 7/2015 | Yamauchi | G01B 21/30 |
| 9,291,442 | B2* | 3/2016 | Hidaka | G01B 21/30 |
| 2018/0209882 | A1 | 7/2018 | Switek, Jr. | |
| 2018/0216962 | A1 | 8/2018 | Tsuji | |
| 2020/0192333 | A1* | 6/2020 | Sato | G05B 19/18 |

FOREIGN PATENT DOCUMENTS

| | | | |
|---|---|---|---|
| JP | 2010112754 | A | 5/2010 |
| JP | 5098995 | B2 | 12/2012 |
| JP | 5369944 | B2 | 12/2013 |
| JP | 5724161 | B2 | 5/2015 |
| JP | 5958392 | B2 | 8/2016 |
| JP | 6245183 | B2 | 12/2017 |
| JP | 2018017579 | A | 2/2018 |
| UA | 90314 | U | 5/2014 |
| WO | 2013038837 | A1 | 3/2013 |

OTHER PUBLICATIONS

International Search Report and Written Opinion for International Application No. PCT/US2019/067522, dated Apr. 8, 2020, 13 pages.

Stephens et al., "Mechanical Property Evaluation and Failure Analysis of Cantilevered LIGA Nickel Microposts" Journal of Microelectromechanical Systems, 2001, vol. 10, No. 3, pp. 347-359.

Zhang et al., "A Piezoelectric-based Infinite Stiffness Generation Method for Strain-Type Load Sensors", Measurement Science and Technology, 2015, vol. 25, 10 pages.

International Preliminary Report on Patentability for International Application No. PCT/US2019/067522, dated Jun. 16, 2021, 9 pages.

PID Section Exponent Software Help Menu, Stable Micro Systems Ltd., 2007, 1 page.†

Table-Top Universal Testing Instruments EZ Test, Shimadzu, 2016, 20 pages.†

Testing Solutions for the Food Industry, Instron, 2003, 12 pages.†

Repka et al., "Temperature Stability and Bioadhesive Properties of Delta9-Tetrahydrocannabinol Incorporated Hydroxypropylcellulose Polymer Matrix Systems", Drug Delivery and Industrial Pharmacy, Jan. 2006, 19 pages.†

Tobyn et al., "Use of a TA.XT2 Texture Analyser in Mucoadhesive Research", International Lambate, 1994, 3 pages.†

Cal State University Purchase Order & Shipping Record, May 2018, 3 pages.†

First Solar Connect Purchase Order & Shipping Record, May 2018, 5 pages.†

NC State University Purchase Order & Shipping Record, May 2018, 5 pages.†

Stable Micro Systems Brochure, Mar. 2018, www.stablemicrosystems.com, 16 pages.†

Zwick Roell Brochure, Zwick Materials Testing, May 2014, 4 pages.†

Calibrate Frame Stiffness, 2007, Stable Micro Systems Ltd., 3 pages.†

Manual for Calibration & Verification of Calibration, Jun. 2003, Texture Technologies Corp, 15 pages.†

Stable Micro Systems Brochure, Dec. 2014, www.stablemicrosystems.com, 12 pages.†

TA.XT.plus Texture Analyser Brochure, Nov. 2001, www.stablemicrosystems.com, 15 pages.†

\* cited by examiner
† cited by third party

TEXTURE ANALYZER

CROSS REFERENCE TO RELATED APPLICATIONS

This application claims priority to U.S. Provisional Patent Application No. 62/782,878, filed Dec. 20, 2018, the contents of such application being incorporated by reference herein.

BACKGROUND OF THE INVENTION

Texture analysis concerns the measurement of the mechanical properties of a product, often a food product, as they relate to its sensory properties detected by humans. Fifty years of texture research has developed a set of definitions relating the sensory properties of a product to the instrumental properties which can be calculated from the results of a two cycle texture profile analysis test. Texture analyzers perform these test by applying controlled forces to the product and recording the product's response in the form of force, deformation, and time.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

In the following detailed description, numerous specific details are set forth by way of examples in order to provide a thorough understanding of the relevant teachings. However, it should be apparent to those skilled in the art that the present teachings may be practiced without such details. In other instances, description of well-known methods, procedures, components, and circuitry are set forth at a relatively high-level, without detail, in order to avoid unnecessarily obscuring aspects of the present teachings.

This description of the exemplary embodiments that follows is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both removable or rigid attachments or relationships, unless expressly described otherwise.

The term "on" means directly supported by an element or indirectly supported by the element through another element integrated into or supported by the element.

Additional objects, advantages and novel features of the examples will be set forth in part in the following description, and in part will become apparent to those skilled in the art upon examination of the following and the accompanying drawings or they may learn by production or operation of the examples. The methodologies, instrumentalities and combinations particularly pointed out in the appended claims assist in realizing and ascertaining the objects and advantages of the present subject matter.

Figure 1A:
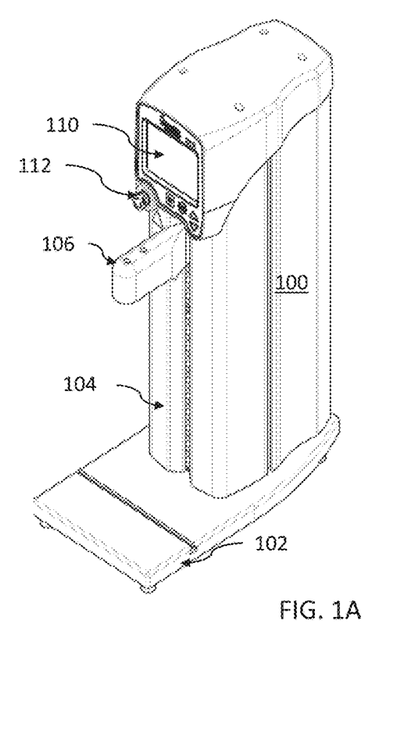
FIG. 1A is a perspective view of a texture analyzer.
Figure 1B:
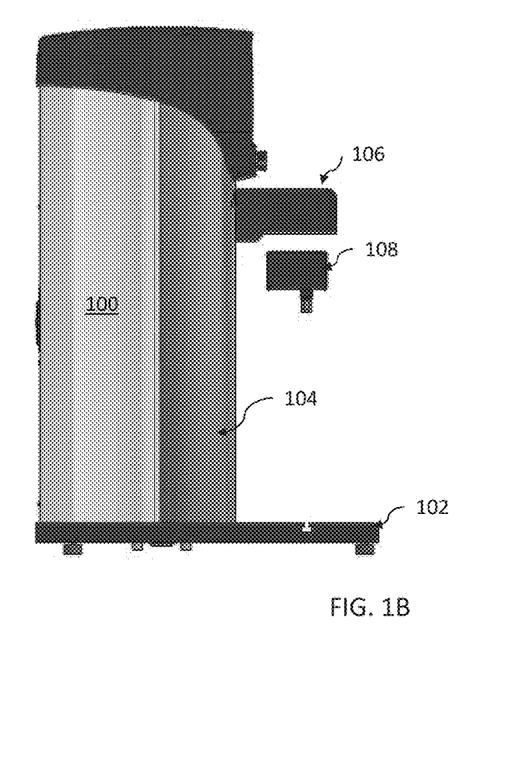
FIG. 1B is a side view of the texture analyzer of FIG. 1A and a load cell for insertion in the texture analyzer.

FIGS. 1A and 1B depict a perspective view and a side view, respectively, of a texture analyzer 100. The texture analyzer 100 includes include a support structure having a base plate 102, a carriage support 104, and a moveable carriage 106. The moveable carriage is adapted to receive a replaceable load cell modules 108 and to move the receive load cell module 108 relative to the base plate 102. The load cell modules 108 can be selected based on the product sample being tested and the type of test being performed on the product sample. Each load cell module 108 has its own deflection characteristics that are unique to that load cell module. These deflection characteristics are determined using a load analyzer and stored for later use.

The texture analyzer 100 includes a display 110 for displaying information such as set up information and test measurements. The texture analyzer 100 additionally includes user controls 112 for setting up and adjusting the texture analyzer 100.

Figure 2:
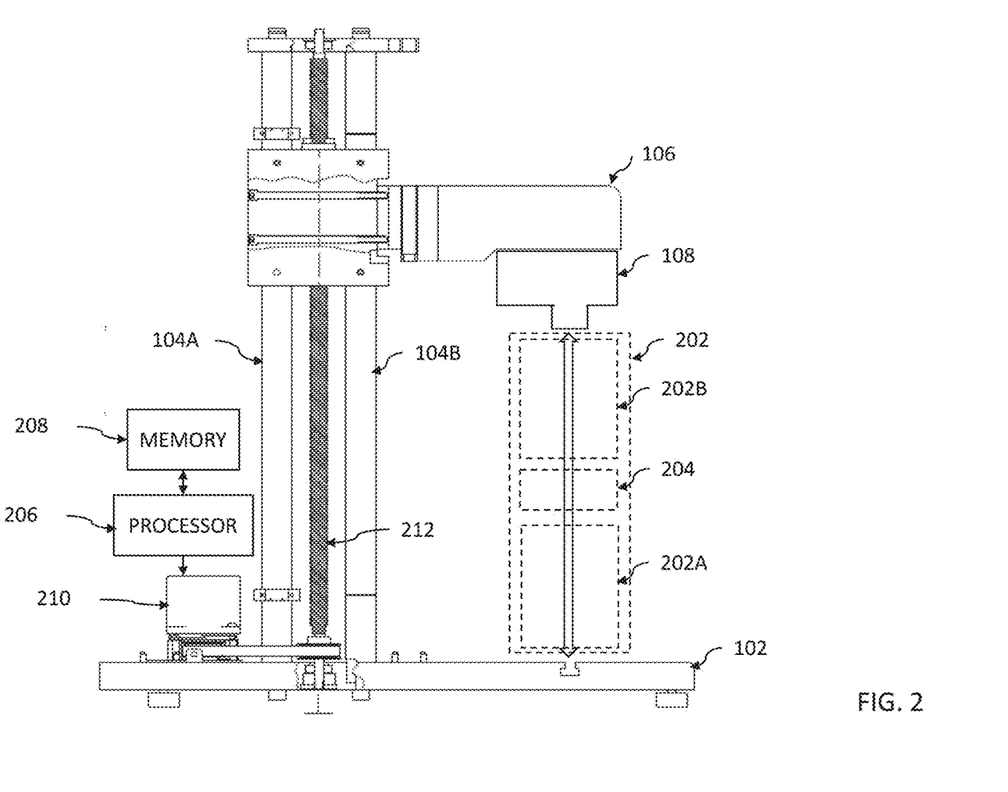
FIG. 2 is a side view of the texture analyzer of FIGS. 1A and 1B with the exterior housing removed, the load cell inserted, and a dashed representation of where a fixture and a sample are positioned in order to analyze the sample.

FIG. 2 depicts the texture analyzer of FIGS. 1A and 1B with the exterior housing removed. A fixture 202 is positioned between the load cell module 108 and the base plate 102 and is designed to facilitate a particular test of a particular product type. The fixture 202 may include a sample support 202A positioned on the base plate 202 and/or an end effector 202B positioned on the load cell module.

In use, a sample 204 is positioned within the fixture 202 relative to the base plate 102 and the load cell module 108 received by the moveable carriage 106. The moveable carriage 106 then provides controlled tensile and/or compressive loads to the sample 204 through the load cell module 108 received by the carriage 106 with the appropriate fixture 202 in place and signals are read from the load cell module for use in determining sample characteristics.

Tensile and compressive loads can be measured for a variety of test types by controlling the position, speed of motion and/or the applied load.

A processor 206 controls the tensile and compressive loads to administer tests on the sample 204 and processes readings from the load cell module 108 to characterize the sample. The processor 206 may display results on display 110 (FIG. 1A). Additionally, processor 206 is in communication with memory 208 to retrieve by way of non-limiting example, test parameter information and deflection information for (1) the support structure and (2) the inserted load cell module.

As shown in FIG. 2, the carriage support includes a first vertical rod 104A and a second vertical rod 104B on which the moveable carriage 106 rides. A motor 210 turns a screw 212 that raises and lowers the moveable carriage 106 to apply tensile and compressive forces.

Some of the unique aspects of the texture analyzer relate to (i.) compensating for deflection of the support structure and for deflection of the particular load cell module received by the support structure, (ii.) applying an adjustable single tap infinite impulse response (IIR) filter to limit signal noise in the raw load signal from the load cell module, and (iii.) characterizing an aspect of the sample (e.g., compliance of the sample in mm/Kg) prior to analysis and/or during analysis in real time) for use in controlling the load applied to the sample.

Regarding (i.), known texture analyzers compensate for deflection of the combined support structure and load cell module. It is not known to compensate for deflection of the load cell module itself. Since the load cell modules can be replaced with load cell module of a different type, and each type of load cell module has its own deflection characteristics, superior measurement results can be obtained by compensating for deflection of both the support structure and the specific load cell module received by the carriage of the texture analyzer.

Figure 3:
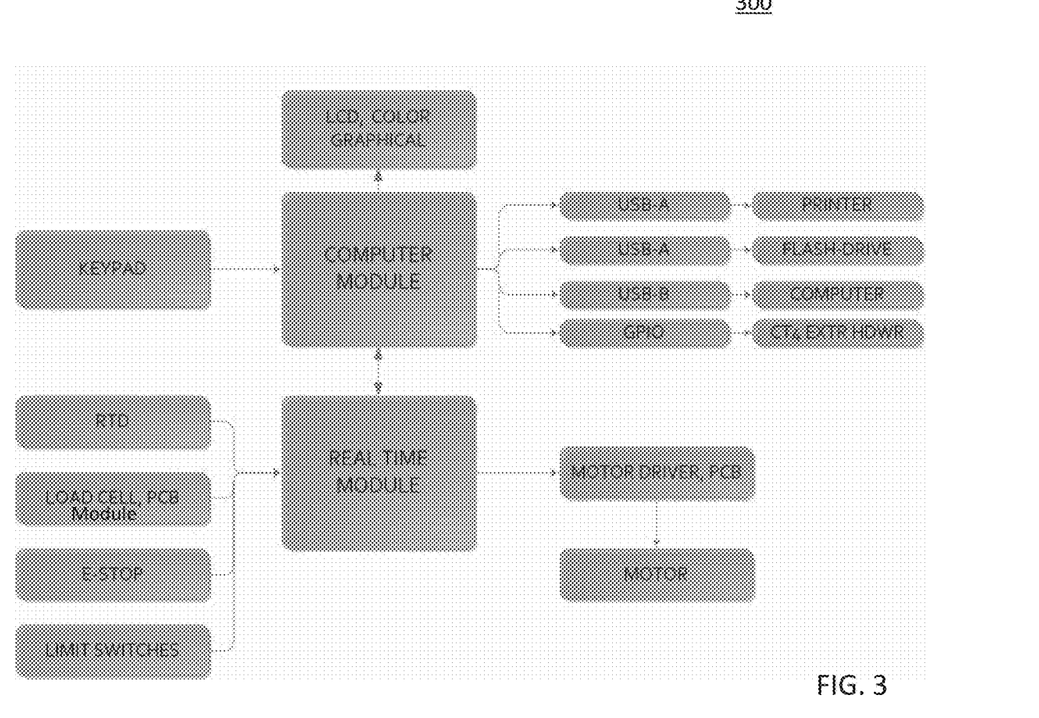
FIG. 3 is a block diagram of electronic components and processing modules for the texture analyzer of FIG. 1A.

FIG. 3 depicts electronic components and processing modules for the texture analyzer of FIG. 1A. The system includes three circuit boards/control modules. These modules are (1.) a load cell module, (2.) a real-time processing module, and (3.) a computer module.

Figure 4:
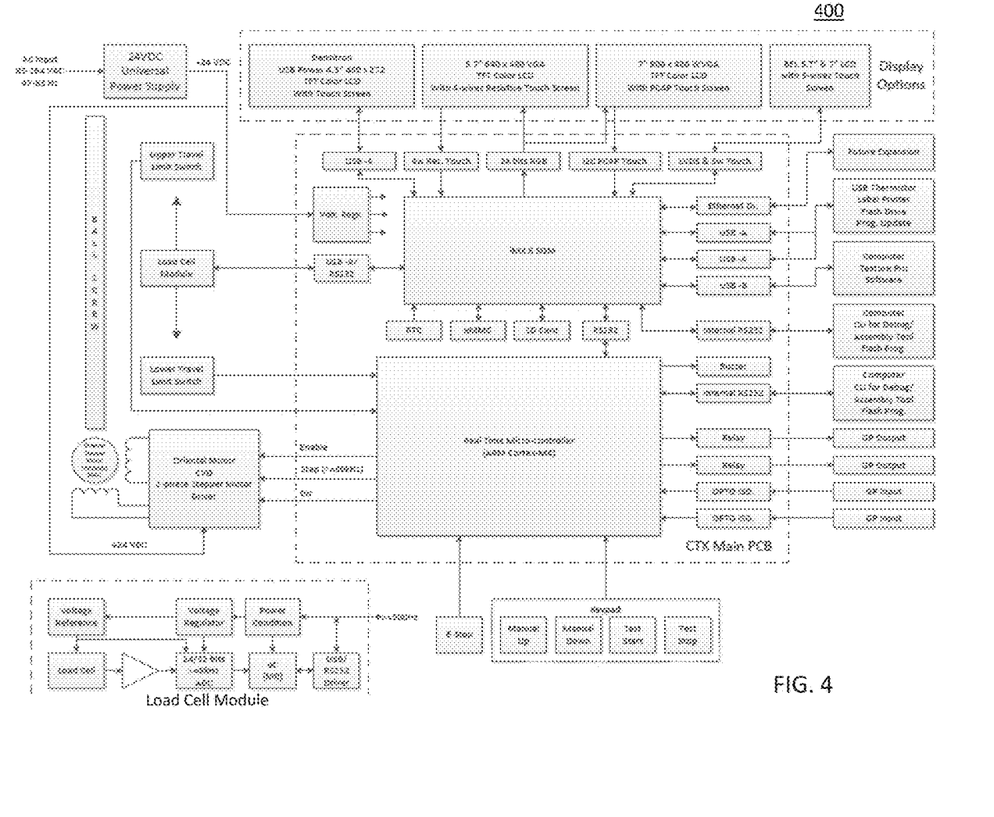
FIG. 4 is a detailed block diagram of the components in FIG. 3.

The load cell module integrates a commercial load cell so it can be calibrated and utilize high-speed digital communications with the real time module. The carriage supports the load cell module and provides an electrical connection. The real time module controls the carriage motion and can adjust the position according to the high-speed load cell data it receives. The computer module provides overall control of the motions and measurements to perform test sequences and provide user and system external interfaces. The detailed system block diagram is shown in FIG. 4.

Deflection compensation:

Total deflection=Load Cell Deflection+Structural Deflection

Load Cell Deflection is calibrated as deflection in mm, according to the full scale load [$L_{FS}$] of the load cell. The calibration can be linear, or another function depending on the actual behavior of the load cell:

Load Cell deflection=$D_{LC}$*[Load[gm]/$L_{FS}$[gm]]

Load=the actual applied load
$L_{FS}$=the full scale load of the load cell
$D_{LC}$=load cell deflection calibration coefficient. For a typical load cell, the linear model is very accurate, $D_{LC}$ is typically 0.2 mm Structural deflection is calibrated with a polynomial, using coefficients based on the maximum design load for the structure [Lmax, e.g. 100 kg]

For convenience, the load and Lmax are in kg. The 3rd order polynomial has the form:

Structural deflection=$Ds3$*[Load[kg]/$L$ max]3+$Ds2$*[Load[kg]/$L$ max]2+$Ds1$*[Load[kg]/$L$ max]

Higher order polynomials are possible, likewise alternate equations for fitting. The critical elements is that the equations can be readily implemented in the LCM/RTM and the superposition of the two deflections can be calculated at high speed to enable accurate control of position.

As the carriage is moved, changes in the applied load cause a deflection in the system. This results in the motor commanded move not matching the actual end-effector motion; the load produced by the sample under test has caused a change in actual position opposite to the load change. The difference in theoretical position and actual position is corrected by commanding an incremental additional motion based on the equation above. The position correction is made multiple times during the execution of a move command.

The compensation can include a term that compensates for changes in system compliance as the carriage moves vertically, and as the temperature changes from temperature at calibration. Temperature compensation may also be useful for the load cell module.

Regarding (ii.), an adjustable single tap IIR filter is applied to help limit signal noise in the raw load signal from the load cell module. The filter is adjustable depending on the test parameters to enable recognition of trends in the load data. Additionally, the filter sensitivity is adjustable to measure brittle, high frequency events. Variable filtering allows the maximum usability of the product, to provide useful measurements over the widest possible range of behaviors at a peak data rate (e.g., 500 Hz).

One "single tap" IIR filter is applied, to help limit the signal noise in the raw load signal. Depending on the test parameters, it may be necessary to adjust the filter to be able to recognize the important trends in the load data. Likewise, for measurements of brittle, high frequency events, the ability to adjust the filter sensitivity is important. Variable filtering allows the maximum usability of the product, to provide useful measurements over the widest possible range of behaviors at the peak data rate [500 Hz]. An example filtering algorithm follows:

$Xn$ filtered=[[1−$b$]*$Xn$]+[$b$*$X(n$−1)filtered]

Xn filtered=filtered value, reported for step n
Were b=filter parameter; Xn=measurement at step n; and
X(n−1)filtered=previous filtered measurement step This allows a single parameter, b, to adjust the influence of the previous measuring point in the weighted average with the current point. Typical values are 0.5<b<1.0. b=0.0 is the trivial case, eliminating any contribution from the previous point, so no filtering is done.

The mechanical system produces accurate movements for the full range of loads. In additional to the pair of vertical rods 104A and 104B, mounted front to back, a set of bushings are configured to adjust to the positions of the rods and eliminate backlash in the linear bearings. The result is a rigid constraint that allows free vertical travel of the carriage without chatter or motion errors.

For some tests, it is desirable to control the applied load, and adjust the position of the force transducer (i.e., the load cell module 108) to maintain the desired load as the sample 204 deforms over time. The texture analyzer 100 and its associated software are configured to characterize the sample and apply the characterization to the control of load.

Due to the wide variety of stiffness in samples, it is difficult to maintain a specific load and/or to control the motion of the load cell module as the sample deflects. When pushing against a very hard sample it is very difficult to stabilize the system. Known texture analyzers set a middle range value for the feed forward. In texture analyzer 100, the texture analyzer 100 and its associated software characterize the sample during the test (e.g., compliance of the sample in mm/Kg) and apply the characterization to control algorithms for applying the load to the sample.

The following algorithm compares the actual load to a desired load and corrects the position to maintain the load for a test interval. This is analogous to applying a fixed load e.g. with a dead weight and measuring the deflection over time to characterize time-based behavior like creep. For stable control of the system, the speed for position corrections is based upon the compliance of the material. The characterization of material can be done with a calibration sample or real time during a test.

$$V \text{ correction} = [\text{Load} - \text{Loadtarget}] * C\text{sample} * TC\text{machine}$$

Where Csample=sample compliance [mm/Kg] and TCmachine=time constant for system.

Good results are achieved for a wide variety of sample materials by determining the sample compliance at Loadtarget.

Figure 5:
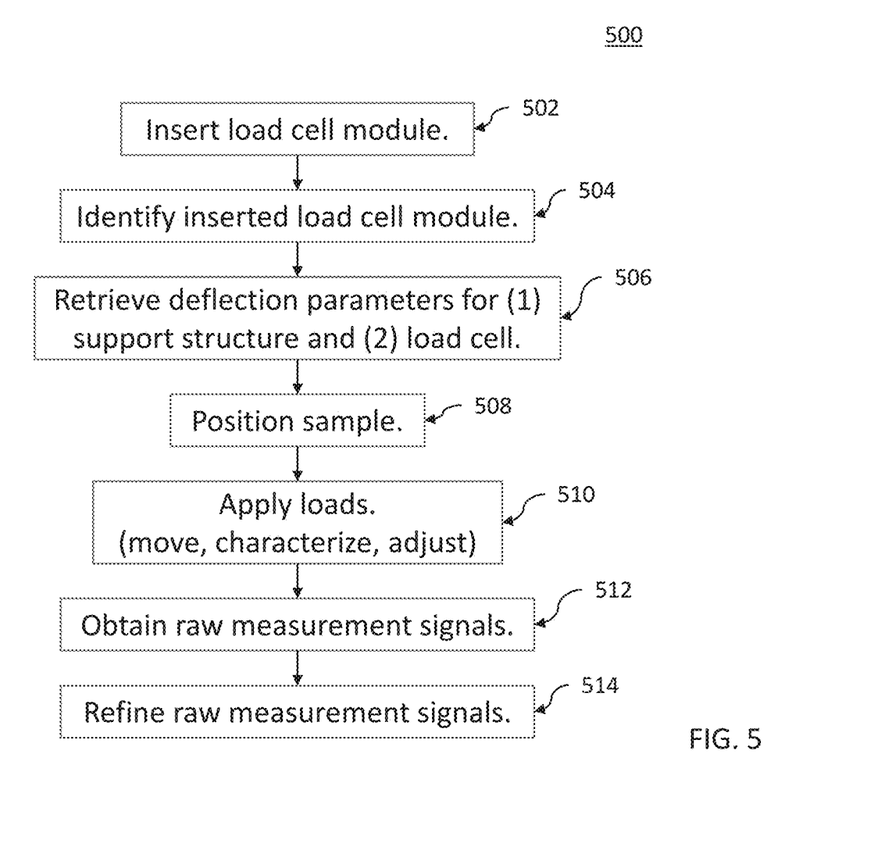
FIG. 5 is a flow chart depicting example steps.

FIG. 5 depicts example steps for analyzing a sample with a texture analyzer.

At step 502, insert a load cell module into a moveable carriage of a texture analyzer support structure.

At step 504, identify the inserted load cell module.

At step 506, retrieve from a memory the texture analyzer support structure deflection parameters and one of a plurality of load cell module deflection parameters stored in a memory of the texture analyzer corresponding to the identified load cell module.

At step 508, position a sample relative to a base plate and the inserted load cell module.

At step 510, apply at least one of tensile loads or compressive loads to the sample through the load cell module.

At step 512, obtain raw measurement signals from the load cell module.

At step 514, refine the raw measurement signals to compensate for deflection in the load cell module using the retrieved one of the plurality of load cell module deflection parameters and to compensate for deflection in the texture analyzer support structure using the retrieved support structure deflection parameters.

Figure 6A:
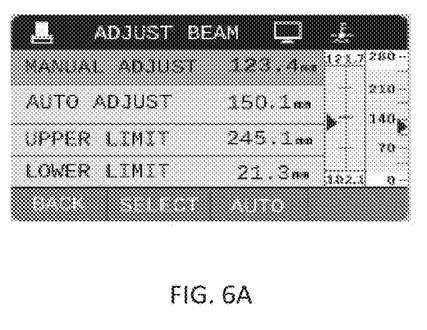
FIG. 6A is a graphical user interface for selecting an adjustment type.

FIG. 6A is a graphical user interface (GUI) for selecting an adjustment type. A user may select the type by first pressing one of "Manual Adjust," "Auto Adjust," "Upper Limit," or "Lower Limit" (which highlights the type of adjustment desired) and, then pressing "Select." If the Manual Adjust is selected, the Manual Adjustment GUI (FIG. 6B) is displayed. "Manual Adjust" is associated with the actual location of the beam. "Auto Adjust" is associated with the standard location of the beam for most test set ups (e.g., the test start position). "Upper Limit" is associated with the upper limit of the travel distance as set by the user (an error may be shown if the beak goes above this setting). "Lower Limit" is associated with the lower limit of the travel distance as set by the user (an error may be shown if the beak goes below this setting. The GUIs of FIGS. 6A and 6B may be displayed on display 110 of the texture analyzer 100.

Figure 6B:
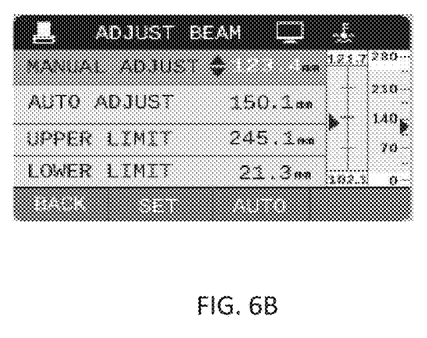
FIG. 6B is a graphical user interface for manual adjustment.

In an example, pressing the up or down arrows causes the beam to move 1 mm. If you press and hold one of the arrows for at least 1.5 seconds, it will start moving the beam faster, up to 10 mm/s. The AUTO key will move the beam at 10 mm/s to the desired location.

While on the SET MANUAL ADJ. screen, pressing the up or down arrows will cause the beam to actually move along with the value within the UPPER LIMIT and LOWER LIMIT settings only.

The SET MANUAL ADJ. screen is shown upon pressing the ADJUST BEAM key by default. Pressing SET will return you to the ADJUST BEAM screen where the limits and auto value can be set.

Pressing AUTO will move the beam to the location specified in AUTO ADJUST. If the location is outside the UPPER/LOWER LIMIT, a TRAVEL ERROR is shown.

Pressing BACK from either the SET MANUAL ADJUST screen or the ADJUST BEAM screen will return the user to the previous screen accessed. This would usually be a CONFIGURE TEST screen or possibly a RESULT screen, but could be MAIN, SETTINGS or SERVICE as well.

The GUI adjustment system enables the operator to set the values on the GUI, and the processor tracks the position to move between these "virtual" stops. This is unlike convention texture analyzers in which mechanical switches and actuators on the device are set by hand.

A GUI may also be presented on display 110 that displays a "virtual scale," which shows the relative position of the carriage, and can display the position of limits of travel set by a user. The scale may be displayed adjacent to the other key information describing tests set-ups and the progress of tests as they are running.

The terms and expressions used herein are understood to have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

What is claimed:

1. A texture analyzer comprising:
   a support structure including a base plate, a carriage support extending from the base plate, and a moveable carriage coupled to the carriage support for movement relative to the base plate, the moveable carriage configured to receive a load cell module;
   a fixture positioned between the base plate and the load cell module, the fixture configured to receive a sample for analysis by the texture analyzer;
   a memory storing support structure deflection parameters and a plurality of load cell module deflection parameters; and
   a processor coupled to the memory, the support structure, and the load cell module when received by the moveable carriage, the processor configured to perform functions including functions to:
      identify the load cell module when received by the moveable carriage;
      retrieve from the memory the support structure deflection parameters and one of the plurality of load cell module deflection parameters corresponding to the identified load cell module;
      obtain raw measurement signals from the load cell module when received by the moveable carriage; and
      refine the raw measurement signals to compensate for deflection in the load cell module using the retrieved one of the plurality of load cell module deflection parameters and to compensate for deflection in the support structure using the retrieved support structure deflection parameters.

2. The texture analyzer of claim 1, wherein the fixture includes at least one of a sample support adjacent the base plate or an effector adjacent the load cell module when received by the moveable carriage.

3. The texture analyzer of claim 1, where the processor is further configured to perform a function to:
   apply an adjustable single tap infinite impulse response (IIR) filter to limit signal noise in the raw measurement signals from the load cell module.

4. The texture analyzer of claim 1, where the processor is further configured to perform a function to:
   move the moveable carriage to apply at least one of compressive or tensile forces to the sample though the load cell module;
   characterize the sample from the refined measurement signals; and
   adjust the movement of the moveable carriage responsive to the characterization of the sample.

5. A method for analyzing a sample, the method comprising the steps of:
   inserting a load cell module into a moveable carriage of a texture analyzer support structure;
   identifying the inserted load cell module;
   retrieving from a memory the texture analyzer support structure deflection parameters and one of a plurality of load cell module deflection parameters stored in a memory of the texture analyzer corresponding to the identified load cell module;
   positioning a sample relative to a base plate and the inserted load cell module;
   applying at least one of tensile loads or compressive loads to the sample through the load cell module;
   obtaining raw measurement signals from the load cell module;
   refining the raw measurement signals to compensate for deflection in the load cell module using the retrieved one of the plurality of load cell module deflection parameters and to compensate for deflection in the texture analyzer support structure using the retrieved support structure deflection parameters.

6. The method of claim 5, wherein the positioning steps comprises positioning the sample within a fixture including at least one of a sample support adjacent the base plate or an effector adjacent the load cell module.

7. The method of claim 5, wherein the refining step further comprises the step of:
   applying an adjustable single tap infinite impulse response (IIR) filter to limit signal noise in the raw measurement signals from the load cell module.

8. The method of claim 5, wherein the applying step comprises the steps of:
   moving the moveable carriage to apply at least one of compressive or tensile forces to the sample though the load cell module;
   characterizing the sample from the refined measurement signals; and
   adjusting the movement of the moveable carriage responsive to the characterization of the sample.

9. The texture analyzer of claim 1, further comprising a user interface coupled to the processor to receive user inputs for setting at least one limit on travel of the moveable carriage, wherein the processor monitors the moveable carriage relative to the set at least one limit.

10. The texture analyzer of claim 9, wherein the user interface displays a virtual scale showing relative position the moveable carriage.

* * * * *